United States Patent
Sharma

[19]

[11] Patent Number: 5,914,134
[45] Date of Patent: Jun. 22, 1999

[54] PROCESS FOR THE PULSATILE DELIVERY OF DILTIAZEM HCL AND PRODUCT PRODUCED THEREBY

[75] Inventor: Vinay K. Sharma, Long Valley, N.J.

[73] Assignee: Wockhardt Europe Limited, Dublin II, Ireland

[21] Appl. No.: 08/788,834

[22] Filed: Jan. 27, 1997

[51] Int. Cl.$^6$ ................................................. A61K 9/16
[52] U.S. Cl. ..................... 424/497; 424/457; 424/458; 424/459; 424/462; 424/468; 424/489; 424/490
[58] Field of Search ................................. 424/497, 490, 424/489, 457, 458, 459, 462, 468, 473; 514/963, 964

[56] References Cited

U.S. PATENT DOCUMENTS

| | | | |
|---|---|---|---|
| 4,960,596 | 10/1990 | Debregeas et al. | 424/458 |
| 4,999,189 | 3/1991 | Kogan et al. | 424/484 |
| 5,213,811 | 5/1993 | Frisbee et al. | 424/493 |
| 5,219,621 | 6/1993 | Geoghegan et al. | 424/462 |
| 5,225,202 | 7/1993 | Hodges et al. | 424/480 |
| 5,260,068 | 11/1993 | Chen | 424/451 |
| 5,286,497 | 2/1994 | Hendrickson et al. | 424/490 |
| 5,288,505 | 2/1994 | Deboeck et al. | 424/497 |
| 5,310,558 | 5/1994 | Pozzi et al. | 424/476 |
| 5,364,620 | 11/1994 | Geoghegan et al. | 424/497 |
| 5,458,888 | 10/1995 | Chen | 424/464 |
| 5,508,040 | 4/1996 | Chen | 424/451 |
| 5,567,441 | 10/1996 | Chen | 424/494 |
| 5,582,838 | 12/1996 | Rork et al. | 424/472 |
| 5,629,017 | 5/1997 | Pozzi et al. | 424/476 |

*Primary Examiner*—Robert H. Harrison
*Attorney, Agent, or Firm*—Schwegman, Lundberg, Woessner, and Kluth, P.A.

[57] ABSTRACT

A drug delivery system for diltiazem-HCl comprises:
a blend of fast, medium and slow release fractions of a multi-layered diltiazem bead substrate, the fast release fraction comprised of a diltiazem bead substrate layered with a polymeric membrane coating having a membrane coating weight gain of from 14 to 18 percent, the medium release fraction comprised of a diltiazem bead substrate layered with a polymeric membrane coating having a membrane coating weight gain of from 39 to 43 percent, and the slow release fraction comprised of diltiazem bead substrate layered with polymeric membrane coating having a membrane coating weight gain of from 63 to 67 percent, wherein at least one of the polymeric membrane coatings comprises a water-insoluble, slightly permeable polymer and a plasticizer triethyl citrate.

22 Claims, 1 Drawing Sheet

PROCESS FOR THE PULSATILE DELIVERY OF DILTIAZEM HCL AND PRODUCT PRODUCED THEREBY

BACKGROUND OF THE INVENTION (1) Field of the Invention

The present invention relates to a drug delivery system, and, more particularly, to a pulsatile drug delivery system for diltiazem HCl capable of site-specific delivery and pulsatile (bolus) kinetics.

(2) Description of the Prior Art

Several investigators have developed pulsatile drug delivery systems that provide slow and/or fast release of a drug based upon physical conditions such as pH, temperature, ionic strength, glucose concentration of metabolites (U.S. Pat. No. 5,226,902); use expandable core material that can be released at specific sites over a period of time (U.S. Pat. No. 4,649,043); or employ an orificed wall constructed of an elastomer that stretches under pressure as osmotic infusion progresses (U.S. Pat. No. 5,221,278).

Publications report development of programmable pulsatile drug delivery systems from an erodible association polymer system and a multi-laminate sample design with alternating drug-loaded layers that deliver a drug only when and where it is needed, at the minimum dose level required to elicit therapeutic results. (Pharmaceutical Research, Vol. 16, No. 8, 1993. "Programmable Drug Delivery from an Erodible Association Polymer System", Xin Xu and Ping I. Lee.) Other report use of hydrophobic material and surfactant that allows for rapid drug release after a predetermined lag time, (Journal of Controlled Release, Vol. 31 1994, 99–108. "The Time Clock System: a New Oral Dosage Form for Fast and Complete Release of Drug after a Predetermined Time", F. Pozzi, P. Furlani, A. Gazzaniga, S. S. Davis, I. R. Wilding.)

Still others report that, by varying the thickness of the film, drug release after the lag period can be enhanced by electrostatic or other physiochemical interactions between the polymer and organic acids.

These investigators have included organic acids such as succinic acid, in order to design a drug delivery system that provides pulsatile kinetics of drug release. (Pharmaceutical Research, Vol. 11, No. 1, 1994, "An Organic Acid-Induced Sigmoidal Release System for Oral Controlled-Release Preparations", S. Narisawa, M. Nagata, C. Danyoshi, H. Yoshino, K. Murata, Y. Hirakawa, and K. Noda.) However, the use of such gastro-irritants and the chronic exposure of the gastric mucosa to such materials can create a potential for mucosal damage.

Several patents have been granted with regard to a controlled release diltiazem formulation for once-a-day dosage—e.g. U.S. Pat. No. 4,894,240, No. 5,286,497, and No. 5,364,620.

All of these patents describe the use of extraneous insolubles in the diltiazem core. These insolubles include organic acids such as fumaric acid, succinic acid, malic acid and adipic acid, as well as lubricants such as talc, sodium stearate, magnesium stearate, and stearic acid. The presence of the organic acids can have a deliterious effect in the gastrointestal tract. Additionally, the controlled release formulation did not permit efficacious drug delivery while providing rate-controlled delivery of drug molecules at the site of absorption in the G.I. Tract.

OBJECTS OF THE PRESENT INVENTION

An object of the present invention is to provide a process for the pulsatile delivery of diltiazem HCl, for drug delivery in a site-specific manner.

Another object of the present invention is to produce a pulsatile delivery of diltiazem HCl in the absence of organic acids.

Another object of the present invention is to produce a pulsatile delivery of diltiazem by having an early duodenal pulse, a medium ileal pulse, and a delayed colonic-specific pulse at time-controlled rates.

Another object of the present invention is to provide a pulsatile delivery of diltiazem HCl having rapid gastric emptying, regardless of prandial state.

Another object of the present invention is to provide a drug delivery system for diltiazem HCl based on gastroduodenal transit time, small intestinal transit time, and colonic transit time, for the most effective delivery of diltiazem HCl.

Another object of the present invention is to provide enhanced bioavailability of diltiazem HCl in humans.

Still another object of the present invention is to deliver diltiazem HCl over a 24 hour period in time-dependent, site-specific reliable manner.

SUMMARY OF THE INVENTION

These and other objects of the present invention are achieved by a formulation of a fast release fraction, a medium release fraction, and a slow release fraction of diltiazem HCl wherein diltiazem cores are layered with polymeric membrane coatings to obtain a fast release fraction having a membrane coating weight gain of 14–18%, a medium release fraction having a membrane coating weight gain of 39–43%, and a slow release fraction having a membrane coating weight gain of 63–67%.

BRIEF DESCRIPTION OF THE DRAWINGS

These and other objects of the present invention will be readily appreciated by reference to the following detailed description when taken with the accompanying drawings, wherein like numerals designate like parts throughout, and wherein.

DETAILED DESCRIPTION OF THE INVENTION

The drug delivery system of the present invention delivers diltiazem HCl in a site-specific, time-controlled manner at the gastrointestinal sites, ie, the duodenum, the ileum, and the colon. In the duodenal site, there is a high rate of absorption and a short residence time (less than one hour). In the ileal site, there is a medium rate of absorption and long residence time (about three hours). In the colonic site, there is a low rate of absorption and longer residence time (about 12 hours). Accordingly, the time-controlled delivery of the drug to the duodenal, ileal, and colonic sites achieves a pulsatile release kinetics, particularly where diltiazem (due to intentinal metabolism/first pass effect) is biotransformed faster when the drug is delivered in a pulsatile manner, leading, therefore, to higher drug concentration in the blood at given dosages.

A fast release fraction of diltiazem HCl is prepared by forming multilayers of a membrane coating dispersion on the drug bead substrate with a weight gain of from 14 to 18%, preferably 15 to 17% and, more particularly, 16%. The membrane coating dispersion is comprised of a water insoluble, slightly permeable, non-enteric polymer compound such as the acrylic resins comprising copolymers of acrylic and methacrylic esters with a low content of quaternary ammonium group, sold under the trademark Eudragit RS, described in the brochure of Messrs. Rohm Pharma. GmbH (1985). The Eudragit RS is slightly permeable. In addition to said polymeric compound in the membrane coating dispersion are plasticizers such as triethyl citrate and antiadherents such as silicone dioxide and talc, thoroughly mixed in water.

After multilayering with the membrane coating dispersion, the membrane coated beads are finish-coated with an Opadry/water dispersion (10% w/w). The beads are then dried and subjected to dehydrothermal treatment at from 45 to 50° C. for 24 hours to complete membrane formation by removing excess moisture.

A medium release fraction of diltiazem HCl is similarly prepared by forming a multilayer of a membrane coating dispersion on the drug bead substrate; however, the weight gain is from 39 to 43%, preferably 40 to 42% and, more particularly, 41%. The resulting medium release beads are finish coated and likewise subjected to dehydrothermal treatment.

The slow release fraction of diltiazem HCl is also prepared by forming a multilayer membrane coating on the drug bead substrate, but with a weight gain of from 63 to 67%, preferably 64 to 66%, and more particularly, 65%. The slow release beads are finish coated and subjected to dehydrothermal treatment.

Figure 1:
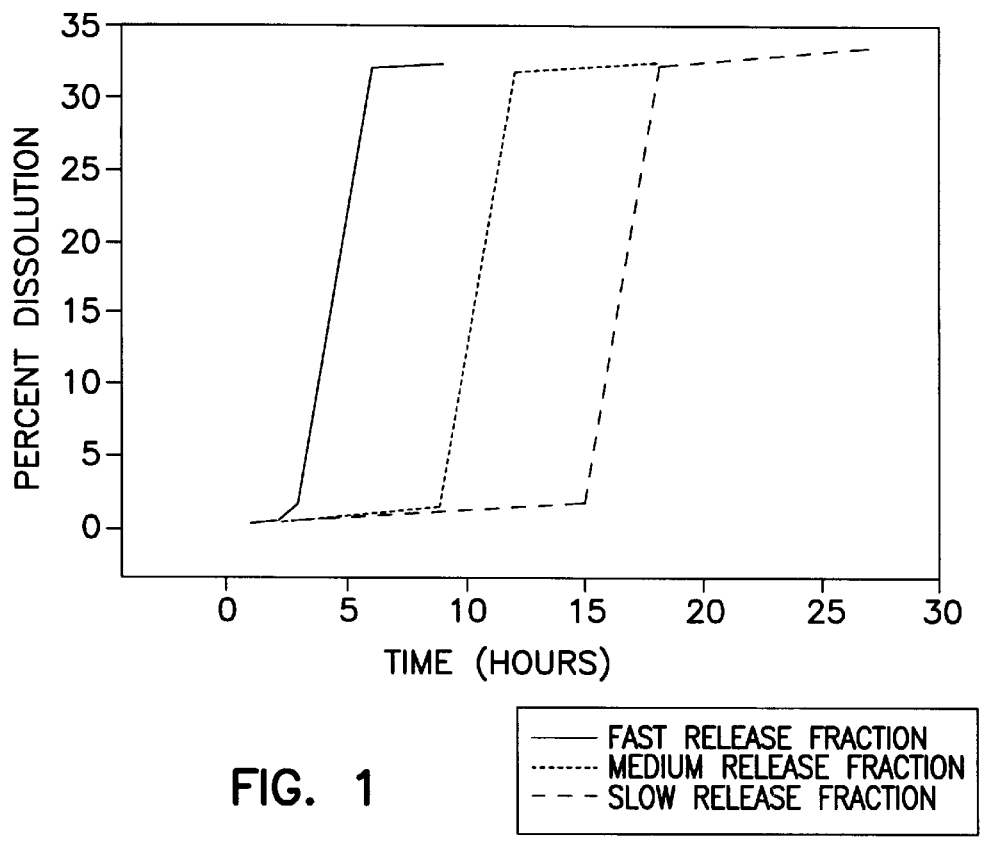
FIG. 1 is a graph of the dissolution profile of each fraction.
Figure 2:
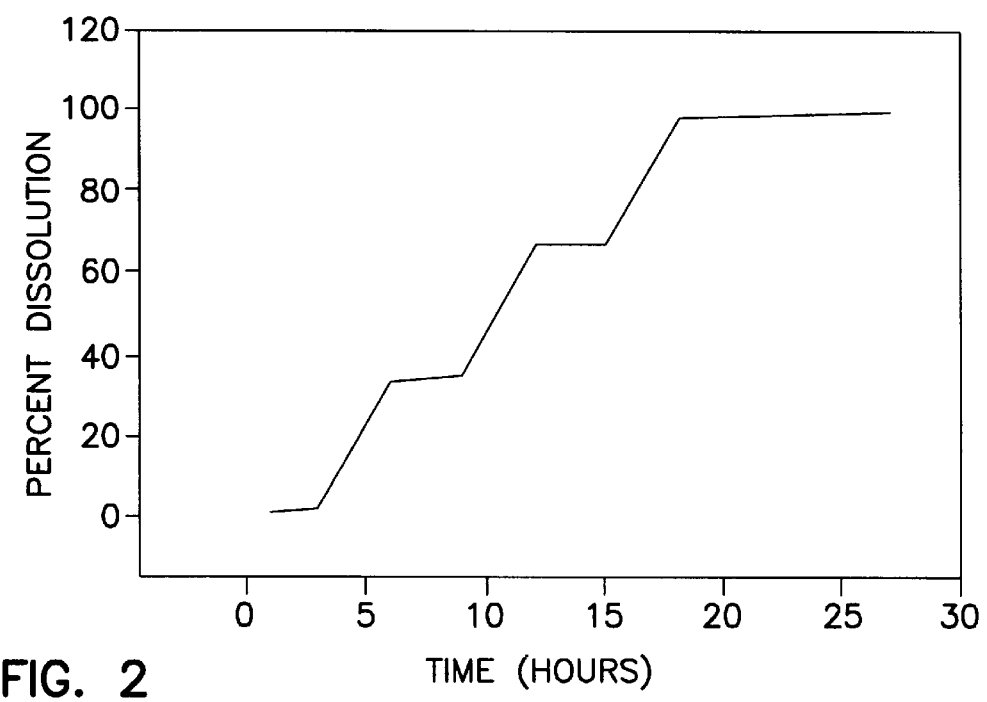
FIG. 2 is a graph of the dissolution profile of the formulation of the present invention.

The drug release system of the present invention is comprised of fast, medium and slow release fractions in a ratio of 33⅓:33⅓:33⅓. FIG. 1 illustrates a dissolution profile of each fraction, whereas FIG. 2 illustrates the combined dissolution profile. The drug release was determined in a Type 2 dissolution apparatus (paddle), according to U.S. Pharmacopoeia XXIII at 37° C. in 0.1N Hcl.

EXAMPLES OF THE PRESENT INVENTION

The preparation process and resulting product of the present invention are described in the following specific examples, which are intended to be merely illustrative, and the present invention is intended not to be limited thereto.

Example I

Preparation of Drug Bead Substrate

The drug layer dispersion is prepared by weighting purified water into a tared container equipped with air mixer/propeller stirrer. With vigorous mixing, hydroxypropylmethyl cellulose (Opadry Y-5-7095) and diltiazem HCl USP are dispersed in water. The dispersion is mixed for 40 minutes until completely suspended; 30/35 mesh nonpareil seeds (Nu-pareil White) are then dispensed into a poly bag-lined vessel. The seeds are then charged into a Wurter Film coater (GPCG-5 7" Wurster HS by Glatt Air Techniques, Ramsey, N.J.).

The fluidization of nonpareils is started at an appropriate volume. The spraying of drug layer dispersion is started at an appropriate spray rate. Inlet temperature, air volume, and spray rate are adjusted to layer drug dispersion effectively onto the seeds. When the dispersion is finished, a subcoat is applied. The subcoat is prepared by dispersing hydroxypropylmethyl cellulose (Opadry YS-307065) in purified water. Total layering operation lasts more than four hours. Actual yield of layered beads is 99%; particle size analysis is as follows:

| Mesh Per cent | 14 | 16 | 18 | 20 | 30 | Pan | Total |
|---|---|---|---|---|---|---|---|
| Retained | 1 | 2 | 94 | 3 | 0 | 0 | 100 |

Example II

Preparation of Fast Release Fraction (FRF)

A fast release fraction having 14 to 18% weight gain on the drug bead substrate is produced by depositing multilayers of a membrane coating dispersion on the drug bead substrate, using a water-insoluble, slightly permeable, non-enteric polymethacrylate compound such as RS (chemically, polyethylacrylate-methyl methacrylate trimethyl ammonium chloride) or poly (EA-MMA-TAMCL, which is available in a 1:2:0.1 ratio.

For preparation of the current invention, as RS 30D Stock Membrane Coating Dispersion is prepared by screening Eudragit RS 30D (30% w/w solids) through a U.S. standard 30 mesh screen into a tared vessel equipped with an air mixer. To the RS 30D is added plasticizer triethyl citrate (TEC) and silicone dioxide (Syloid 244 FP) as an antiadherant, which must be added to prevent agglomeration of RS 30D-coated beads due to significant decrease in the glass transition temperature (T). In another tared container equipped with an air mixer, talc USP is added to purified water. The separately prepared dispersions of RS 30D/TEC/Syloid/water and talc/water are mixed thoroughly.

Next, a division of drug-layered beads and RS 30D (SMCD) is carried out to determine amounts of RS 30D Stock Membrane Coating Dispersion necessary to prepare the FRF and SRF components of the final product.

First, the quantity of layered drug beads (calculated for FRF) is dispersed into the Wurster film coater (GPCG-5 7" Wurster HS by Glatt). Using an appropriate air volume, inlet temperature and spray rate, the designer applies the quantity of RS 30D Stock membrane Coating Dispersion onto the drug-layered beads. When the RS 30D Stock Membrane Coating Dispersion is depleted, sufficient purified water is sprayed at a reduced rate, to clean the nozzle. The water is sprayed for five minutes while adjusting coating parameters for the subsequent Opadry finish coat. Opadry dispersion (10% w/w) is sprayed onto membrane-coated beads at an appropriate spray rate, air volume and inlet temperature. When the Opadry finish coat application is completed, the product (FRF) is dried at current parameters for five minutes, and then discharged and reconciled. Actual yield of the membrane-coated beads (FRF) is 99% and particle size analysis is as follows:

| Mesh Per cent | 14 | 16 | 18 | 20 | 30 | Pan | Total |
|---|---|---|---|---|---|---|---|
| Retained | 1 | 43 | 55 | 1 | 0 | 0 | 100 |

Example III

Preparation of Medium Release Fraction

A quantity of layered drug beads (calculated for MRF) are dispensed into the Wurster film coater (GPCG-5 7" Wurster HS by Glatt). The process employed for preparation of the FRF is repeated for the MRF. Actual yield of the membrane-coated beads (MRF) is 98%; particle size analysis is as follows:

| Mesh Per cent | 14 | 16 | 18 | 20 | 30 | Pan | Total |
|---|---|---|---|---|---|---|---|
| Retained | | 68 | 31 | 1 | 0 | 0 | 100 |

Example IV

Preparation of Slow Release Fraction (SRF)

A quantity of layered drug beads (calculated for SRF) are dispensed into the Wurster film coater (GPCG-5 7" Wurster HS by Glatt). The process employed for preparation of FRF was repeated for SRF. Actual yield of the membrane-coated beads (SRF) is 98%; particle size analysis is as follows:

| Mesh Per cent | 14 | 16 | 18 | 20 | 30 | Pan | Total |
|---|---|---|---|---|---|---|---|
| Retained | 1 | 94 | 5 | 0 | 0 | 0 | 100 |

Example V

Dehydrothermal Treatment

The fast, medium and slow release fractions are given dehydrothermal treatment at 45–50 degrees C. for 24 hours in a forced-air oven, to complete the membrane formation process by removing excess moisture.

Example VI

Drug Delivery System

In a triple-filling process, the fast, medium and slow release fractions are filled in the same capsule, in a ratio of 33⅓, 33⅓, and 33⅓. Furthermore, the desirable release profile will be obtained if the weight gain of individual fractions (FRF, MRF and SRF) are controlled within narrow limits, such as 15–17 (FRF), 39–41 (MRF), and 63–65 for SRF.

Example VII

|  | Mg/ capsule | Batch Quantities (20,000 capsules) (kg) |
|---|---|---|
| Diltiazem HCL, USP | 300.0 | 6.0 |
| Nupareil sugar sphere | 85.0 | 1.7 |
| Hydroxypropylmethyl Cellulose | 33.71 | 0.674 |
|  | 418.71 | 8.374 |
| RS 30D (Dry Basis) | 3.000 | |
| Triethyl Citrate | 0.600 | |
| Talc, USP | 0.600 | |
| Syloid 244FP | 0.030 | |
|  | 4.230 | |

In order to prepare a batch of 20,000 capsules, a 4% w/w dispersion of hydroxypropylmethyl cellulose (HPMC) was prepared in water using a Lightnin Mixer (equipped with an impeller). Then, 6.0 kg of diltiazem hydrochloride was slowly suspended in the HPMC dispersion. The preparation of the dispersions was mixing these ingredients at a controlled RPM.

Then the HPMC/Diltiazem Hcl dispersion was pumped through a calibrated, peristaltic pump to deliver the HPMC/Diltiazem dispersion to fluidized Nu-Pareil white core substrate at an appropriate air volume. The HPMC/Diltiazem Hcl dispersion was sprayed at an appropriate spray rate. The inlet air temperature, air volume, and spray rate was adjusted to effectively layer the entire HPMC/Diltiazem Hcl dispersion on to Nu-Pareil white core substrate. Then, a sub-coat of a proprietary HPMC (Opadry® YS-3 7065) was applied to layered drug beads in order to, theoretically, provide a weight gain of one, using fluidized film coating equipment.

A stock dispersion of membrane coat was prepared by plasticizing RS 30D (10 kg of 30% w/w dispersion in water) with 20% of the plasticizer triethyl citrate (TEC), 20 percent of talc, and 1 percent of Syloid 244 FP, based on the amount of RS 30D on a dry basis. The membrane coat dispersion was applied to provide a 16% (fast release fraction), 39% (medium release fraction), and 63% (slow release fraction) weight gain, respectively, using the fluidized film coating equipment.

Then, a sub-coat of a proprietary HPMC (Opadry® YS-3 7065) was applied to the membrane coated beads in order to, theoretically, provide a weight gain of 2 percent, using fluidized film coating equipment.

What is claimed:

1. A drug delivery system for diltiazem-HCl, which comprises:
   a blend of fast, medium and slow release fractions of a multi-layered diltiazem bead substrate, said fast release fraction comprised of a diltiazem bead substrate layered with a polymeric membrane coating having a membrane coating weight gain of from 14 to 18 percent, said medium release fraction comprised of a diltiazem bead substrate layered with a polymeric membrane coating having a membrane coating weight gain of from 39 to 43 percent, and said slow release fraction comprised of diltiazem bead substrate layered with a polymeric membrane coating having a membrane coating weight gain of from 63 to 67 percent, wherein at least one of said polymeric membrane coatings comprises a water-insoluble, slightly permeable polymer and a plasticizer comprising triethyl citrate.

2. The drug delivery system for diltiazem.HCl as defined in claim 1, wherein said fast release fraction has a membrane coating weight gain of from 15 to 17 percent, said medium release fraction having a membrane coating weight gain of from 40 to 42 percent and said slow release fraction having a membrane coating weight gain of from 64 to 66 percent.

3. The drug delivery system for diltiazem.HCl as defined in claim 2, wherein said fast release fraction has a membrane coating weight gain of 16 percent, said medium release fraction having a membrane coating weight gain of 41 percent and said slow release fraction having a membrane coating weight gain of 65 percent.

4. The drug delivery system for diltiazem.HCl as defined in claim 1 wherein each of said release fractions are released in less than three (3) hours, from the beginning of drug release.

5. A method of treating cardiovascular disorders with a diltiazem-Hcl formulation suitable for a once-a-day oral administration comprising:
   administering an effective amount of diltiazem-HCl formulation having a fast release fraction, a medium release fraction and a slow release fraction, said fast release fraction comprised of a diltiazem bead substrate layered with a polymeric membrane coating having a membrane coating weight gain of from 14 to 18 percent, said medium release fraction comprised of a diltiazem bead substrate layered with a polymeric membrane coating having a membrane coating weight gain of from 39 to 43 percent, and said slow release fraction comprised of diltiazem bead substrate layered with a polymeric membrane coating having a membrane coating weight gain of from 63 to 67 percent, wherein at least one of said polymeric membrane coatings comprises a water-insoluble, slightly permeable polymer and a plasticizer comprising triethyl citrate.

6. The method of treating cardiovascular disorders as defined in claim 5 wherein said fast release fraction has a membrane coating weight gain of from 15 to 17 percent, said medium release fraction having a membrane coating weight gain of from 40 to 42 percent and said slow release fraction having a membrane coating weight gain of from 64 to 66 percent.

7. The method of treating cardiovascular disorders as defined in claim 6 wherein said fast release fraction has a membrane coating weight gain of 16 percent, said medium release fraction having a membrane coating weight gain of 41 percent and said slow release fraction having a membrane coating weight gain of 65 percent.

8. The method of treating cardiovascular disorders as defined in claim 5 wherein said diltiazem.HCl formulation exhibits the following in-vitro dissolution pattern when measured in a type 2 dissolution apparatus, according to U.S. Pharmacopia XXIL, in 0.1N HCL at 100 rpm;
  (a) from zero to 33 percent of total diltiazem is released after six (6) hours of measurement in said apparatus;
  (b) from 33 to 66 percent of total diltiazem is released after twelve (12) hours of measurement in said apparatus; and
  (c) from 66 to 100 percent is released after eighteen (18) hours of measurement in said apparatus.

9. A drug delivery system for diltiazem-HCl, which comprises:
  a blend of fast, medium and slow release fractions of a multi-layered diltiazem bead substrate, said fast release fraction comprised of a diltiazem bead substrate layered with a polymeric membrane coating having a first membrane coating weight gain, said medium release fraction comprised of a diltiazem bead substrate layered with a polymeric membrane coating having a second membrane coating weight gain, and said slow release fraction comprised of diltiazem bead substrate layered with a polymeric membrane coating having a third membrane coating weight gain, wherein at least one of said polymeric membrane coatings comprises a water-insoluble, slightly permeable polymer and a plasticizer comprising triethyl citrate, and said third membrane coating weight gain is greater than said second membrane coating weight gain, and said second membrane coating weight gain is greater than said first membrane coating weight gain.

10. The drug delivery system of claim 1 wherein all polymeric membrane coatings comprise a water-soluble, slightly permeable polymer and a plasticizer comprising triethyl citrate.

11. The drug delivery system of claim 9 wherein all polymeric membrane coatings comprise a water-insoluble, slightly permeable polymer and a plasticizer comprising triethyl citrate.

12. The drug delivery system of claim 1 wherein all polymeric membrane coatings comprise a water-insoluble, slightly permeable polymer, silica and a plasticizer comprising triethyl citrate.

13. The drug delivery system of claim 9 wherein all polymeric membrane coatings comprise a water-insoluble, slightly permeable polymer, silica and a plasticizer comprising triethyl citrate.

14. The drug delivery system of claim 1 wherein said diltiazem is present as a layer within a bead and said layer within which said diltiazem is present consists essentially of diltiazem and a binder.

15. The drug delivery system of claim 9 wherein said diltiazem is present as a layer within a bead and said layer within which said diltiazem is present consists essentially of diltiazem and a binder.

16. The drug delivery system of claim 10 wherein said diltiazem is present as a layer within a bead and said layer within which said diltiazem is present consists essentially of diltiazem and a binder.

17. The drug delivery system of claim 11 wherein said diltiazem is present as a layer within a bead and said layer within which said diltiazem is present consists essentially of diltiazem and a binder.

18. The drug delivery system of claim 12 wherein said diltiazem is present as a layer within a bead and said layer within which said diltiazem is present consists essentially of diltiazem and a binder.

19. The drug delivery system of claim 13 wherein said diltiazem is present as a layer within a bead and said layer within which said diltiazem is present consists essentially of diltiazem and a binder.

20. A drug delivery system for diltiazem-HCl, which comprises:
  a blend of fast, medium and slow release fractions of a multi-layered diltiazem bead substrate, said fast release fraction comprised of a diltiazem bead substrate layered with a polymeric membrane coating having a membrane coating weight gain of from 14 to 18 percent, said medium release fraction comprised of a diltiazem bead substrate layered with a polymeric membrane coating having a membrane coating weight gain of from 39 to 43 percent, and said slow release fraction comprised of diltiazem bead substrate layered with a polymeric membrane coating having a membrane coating weight gain of from 63 to 67 percent, wherein at least one of said polymeric membrane coatings comprises a water-insoluble, slightly permeable polymer, a plasticizer comprising triethyl citrate, and an antiadherent selected from the group consisting of silica and talc, and beads of each fraction having an enteric coating layer over said polymeric membrane coatings.

21. A drug delivery system for diltiazem-HCl, which comprises:
  a blend of fast, medium and slow release fractions of a multi-layered diltiazem bead substrate, said fast release fraction comprised of a diltiazem bead substrate layered with a polymeric membrane coating having a membrane coating weight gain of from 14 to 18 percent, said medium release fraction comprised of a diltiazem bead substrate layered with a polymeric membrane coating having a membrane coating weight gain of from 39 to 43 percent, and said slow release fraction comprised of diltiazem bead substrate layered with a polymeric membrane coating having a membrane coating weight gain of from 63 to 67 percent.

22. A method of treating cardiovascular disorders with a diltiazem-HCl formulation suitable for a once-a-day oral administration comprising:

administering an effective amount of diltiazem-HCl formulation having a fast release fraction, a medium release fraction and a slow release fraction, said fast release fraction comprised of a diltiazem bead substrate layered with a polymeric membrane coating having a membrane coating weight gain of from 14 to 18 percent, said medium release fraction comprised of a diltiazem bead substrate layered with a polymeric membrane coating having a membrane coating weight gain of from 39 to 43 percent, and said slow release fraction comprised of diltiazem bead substrate layered with a polymeric membrane coating having a membrane coating weight gain of from 63 to 67 percent.

* * * * *